(12) United States Patent
Satlewal et al.

(10) Patent No.: US 11,028,385 B2
(45) Date of Patent: Jun. 8, 2021

(54) STABLE LIGNOCELLULOLYTIC ENZYME COMPOSITION

(71) Applicants: Indian Oil Corporation Limited, Mumbai (IN); Department Of Biotechnology, New Delhi (IN)

(72) Inventors: Alok Satlewal, Faridabad (IN); Ruchi Agrawal, Faridabad (IN); Ravindra Kumar, Faridabad (IN); Ravi Prakash Gupta, Faridabad (IN); Suresh Kumar Puri, Faridabad (IN); Sankara Sri Venkata Ramakumar, Faridabad (IN)

(73) Assignees: Indian Oil Corporation Limited, Mumbai (IN); Department of Biotechnology, New Delhi (IN)

( * ) Notice: Subject to any disclaimer, the term of this patent is extended or adjusted under 35 U.S.C. 154(b) by 9 days.

(21) Appl. No.: 16/353,533

(22) Filed: Mar. 14, 2019

(65) Prior Publication Data
US 2019/0284545 A1    Sep. 19, 2019

(30) Foreign Application Priority Data
Mar. 14, 2018    (IN) .............................. 201821009341

(51) Int. Cl.
*C12N 9/96*    (2006.01)
*C12N 9/24*    (2006.01)

(52) U.S. Cl.
CPC ................. *C12N 9/96* (2013.01); *C12N 9/24* (2013.01); *C12N 9/2402* (2013.01); *C12Y 302/01004* (2013.01)

(58) Field of Classification Search
CPC .......... C12N 9/96; C12N 9/24; C12N 9/2402; C12Y 302/01004
USPC ...................................................... 424/94.1
See application file for complete search history.

(56) References Cited

U.S. PATENT DOCUMENTS

| | | | |
|---|---|---|---|
| 4,537,706 A * | 8/1985 | Severson, Jr. ...... | C11D 3/38663 510/108 |
| 7,928,052 B2 * | 4/2011 | Lenoir .................. | C11D 3/042 510/119 |
| 2003/0175232 A1 * | 9/2003 | Elliott .................. | A61K 8/0208 424/70.14 |
| 2008/0090276 A1 | 4/2008 | Van Dyck et al. | |

FOREIGN PATENT DOCUMENTS

| | | |
|---|---|---|
| CN | 101381716 | 3/2009 |
| CN | 103740690 | 4/2014 |
| EP | 137615 | 1/1988 |
| EP | 137616 | 1/1988 |
| EP | 160762 | 8/1989 |
| EP | 0633311 | 5/2000 |
| EP | 2383330 | 11/2011 |
| WO | 2003041667 | 5/2003 |
| WO | 2013029170 | 3/2013 |

OTHER PUBLICATIONS

Naika et al. 2009. Effect of Cosolvents on the Structural Stability of Endoglucanase from *Aspergillus aculeatus*. J. Agric. Food Chem. 59: 10450-10456 (Year: 2009).*
Combes et al. 1987. Mechanism of Enzyme Stabilization. Ann. N. Y. Acad. Sci. 501(1): 59-62. (Year: 1987).*
Cassia Pereira et al. 2017. Chapter 6: Effect of Metal Ions, Chemical Agents, and Organic Compounds on Lignocellulolytic Enzyme Activity. In M. Senturk. Enzyme Inhibitors and Activators, (pp. 139-144). Rijeka, Croatia: InTech. (Year: 2017).*
M.A. Clarke. 2003. SYRUPS. Benjamin Caballero. Encyclopedia of Food Sciences and Nutrition (Second Edition). Academic Press. pp. 5711-5717. ISBN 9780122270550. https://doi.org/10.1016/B0-12-227055-X/01175-5. (Year: 2003).*
Chou, T.C. 2006. Theoretical Basis, Experimental Design, and Computerized Simulation of Synergism and Antagonism in Drug Combination Studies. Pharmacological Reviews. 58: 621-581. (Year: 2006).*
He et al., Biotechnol. Biofuels, 7(43):1-9 (2014) (Year: 2014).*
Villena et al., Electron. J. Biotechnol., 10(1):1-8 (2007) (Year: 2007).*
Chong et al., "Stability of endoglucanases from mesophilic fungus and thermohilic bacterium in acidified polyols", Enzyme and Microbial Technology (20154 http://dx.doi.org/doi:10.1016/j.enzmictec.2014.04.2015.
Gunny et al., "Deep Eutectic Solvents-Cellulase system for lignocellulose hydrolysis and analysis of glucose production, energy consumption and kinetic performance", Bioresource Technology (2015) 181:297-302.

* cited by examiner

*Primary Examiner* — Thomas J. Visone
(74) *Attorney, Agent, or Firm* — Melissa M. Hayworth; E. Joseph Gess

(57) ABSTRACT

The present invention relates to a formulation to stabilize lignocellulolytic enzyme mixture. This invention in particular relates to a formulation composed of lignocellulolytic enzyme with critical dosages of molasses either with petrochemical waste or glycerol as an additive to improve enzyme stability in a synergistic manner.

3 Claims, 6 Drawing Sheets

STABLE LIGNOCELLULOLYTIC ENZYME COMPOSITION

PRIORITY

This application claims priority to Indian Patent Application No. 201821009341 filed Mar. 14, 2018 entitled "A Stable Lignocellulolytic Enzyme Composition", the contents of which are hereby incorporated by reference in their entirety.

FIELD OF THE INVENTION

The present invention relates to a formulation to stabilize lignocellulolytic enzyme. This invention in particular relates to a formulation composed of lignocellulolytic enzyme with critical dosages of molasses either with glycerol or petrochemical waste stream as an additive to improve enzyme stability in a synergistic manner.

BACKGROUND

Lignocellulose refers to plant dry matter (biomass) and is the most abundantly available raw material on the Earth. It is composed of carbohydrate polymers (such as cellulose, hemicellulose), and an aromatic polymer (lignin). These carbohydrate polymers contain different sugar monomers (six and five carbon sugars) and they are tightly bound to lignin. From the last few decades, there has been an increasing research interest in the value of lignocellulosic biomass. Lignocellulosic biomass is an inexpensive, renewable, abundant natural resource which is capable of being employed for large-scale and cost-effective bio-energy collection as well as production of value added products, such as biofuels. The effective utilization of lignocellulosic biomass for the production of value-added products mainly depends on their hydrolysis into constituent soluble sugars.

Due to the recalcitrant structure of lignocellulose and heterogeneous nature of pretreated biomass, a consortium of enzymes differing in their specificity and mechanism of action is needed to act on this substrate (like endoglucanases, exoglucanases, xylanases, mannases, esterases, arabinofuranosidases etc.). The main enzymes involved in lignocellulose hydrolysis include cellulases, hemicellulases, lignin modifying enzymes and other helper enzymes/proteins such as Swollenin. Despite the commercial availability of lignocellulolytic enzymes, there are certain challenges in using these enzymes at an industrial scale which arise from their inherent characteristics, such as lack of stability.

Moreover, the high cost of lignocellulolytic enzymes is also a major challenge impacting the economic feasibility of the second generation (2G) bioethanol production from lignocellulosic biomass. Therefore, a new concept is being currently implemented wherein integrated on-site enzyme production occurs along with 2G bioethanol production. Here, cost effective lignocellulosic biomass and other nutrients are utilized as a nutrient/carbon source for enzyme production instead of expensive crystalline cellulose and avicel.

Enzyme supplementation with stabilizing agents or stabilizers is usually recommended to improve enzyme stability and performance. These stabilizers provide resistance to the catalytically active protein structures towards high temperatures, pHs, microbial contamination and other denaturing influences. The selection of the appropriate additive depends on the nature of enzyme i.e. on its hydrophilic or hydrophobic character and the degree of interaction with the additive.

EP0633311B1 describes a process wherein 10% w/w of hydrophobic amines acted as cellulase enzyme stabilizing compounds to formulate liquid detergent compositions. The hydrophobic amine acts as counter ion resulting in the rearrangement of the anionic surfactant to produce a 'shielding-off' effect by the neutral ion pair formation of hydrophobic amine-anionic surfactant in the surfactant phase of the liquid detergent. Similarly, EP160762, EP137615 and EP137616 disclose liquid detergents comprised of cyclohexylamine to stabilize amylase enzyme.

EP2383330A1 describes a method to stabilize enzymes from protease, cellulase, lipase, amylase by using aryl carboxylic acid as an enzyme stabilizer at 20% w/w of liquid detergents. EP 1924677 A1 describes a method to stabilize concentrated liquid enzyme by adding phenyl boronic acid derivative.

WO 2003041667 A2 describes compositions to stabilize proteases with certain osmo-protectants like glycerine, polyethylene glycol (preferably those having an average molecular weight of 200 to 400), hexane, triol, butane-1,4-diol, butoxytriol, erythritol, xylitol and methods for using such compositions in personal care.

US20080090276 describes a heat stable enzyme composition formed by adding the enzymes to sugar syrup and drying the mixture either by spreading it on a carrier or by spray drying.

WO2013029170 describes a fermentation process for producing a cellulase enzyme mixture from *Myceliophthora* and related organisms.

Chong et al. (2015), Enzyme and Microbial Technology, describes the stability of endoglucanases from mesophilic fungus and thermohilic bacterium in acidified polyols.

Gunny et al. (2015), Bioresource Technology, describes Deep Eutectic Solvents-Cellulase system for lignocellulose hydrolysis and analysis of glucose production, energy consumption and kinetic performance.

CN101381716B describes a cellulase enzyme stabilizing agent including 30 to 50 percent of the sucrose, 5 to 15 percent of the sodium chloride, 0.01 to 0.03 percent of the potassium sorbate and 0.01 to 0.02 percent of the sodium hyposulfite.

CN103740690A describes an enzyme (cellulase, lipase, hemicellulase) stabilizing agent composed of diols or triols like ethylene glycol, propanediol, butanediol, pentanediol, glycerol, butanetriol or pentanetriol.

Therefore, there is a need in the art for a lignocellulolytic enzyme composition with improved ambient and operational stability.

SUMMARY

The present disclosure relates to a lignocellulolytic enzyme composition, said composition comprising:
(a) 65% to 85% w/w lignocellulolytic enzyme;
(b) 10% to 15 w/w additive; and
(c) 5% to 20% w/w molasses;
Wherein; the additive is glycerol or a petrochemical waste stream.

DETAILED DESCRIPTION

Figure 1A:
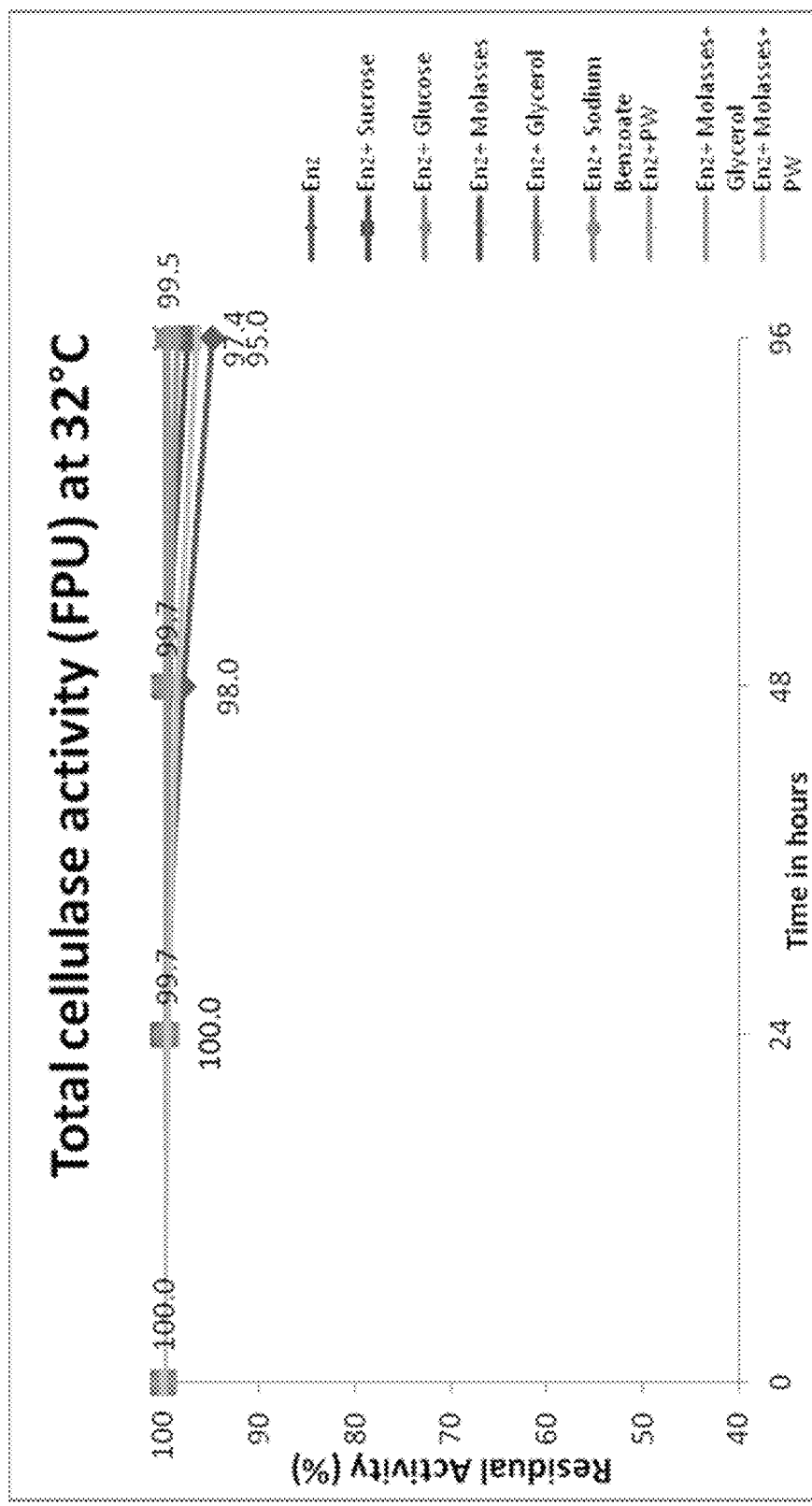
FIG. 1(a) illustrates graphical representation of enzyme stability at ambient temperatures (32° C.) of total cellulase activity.
Figure 1:
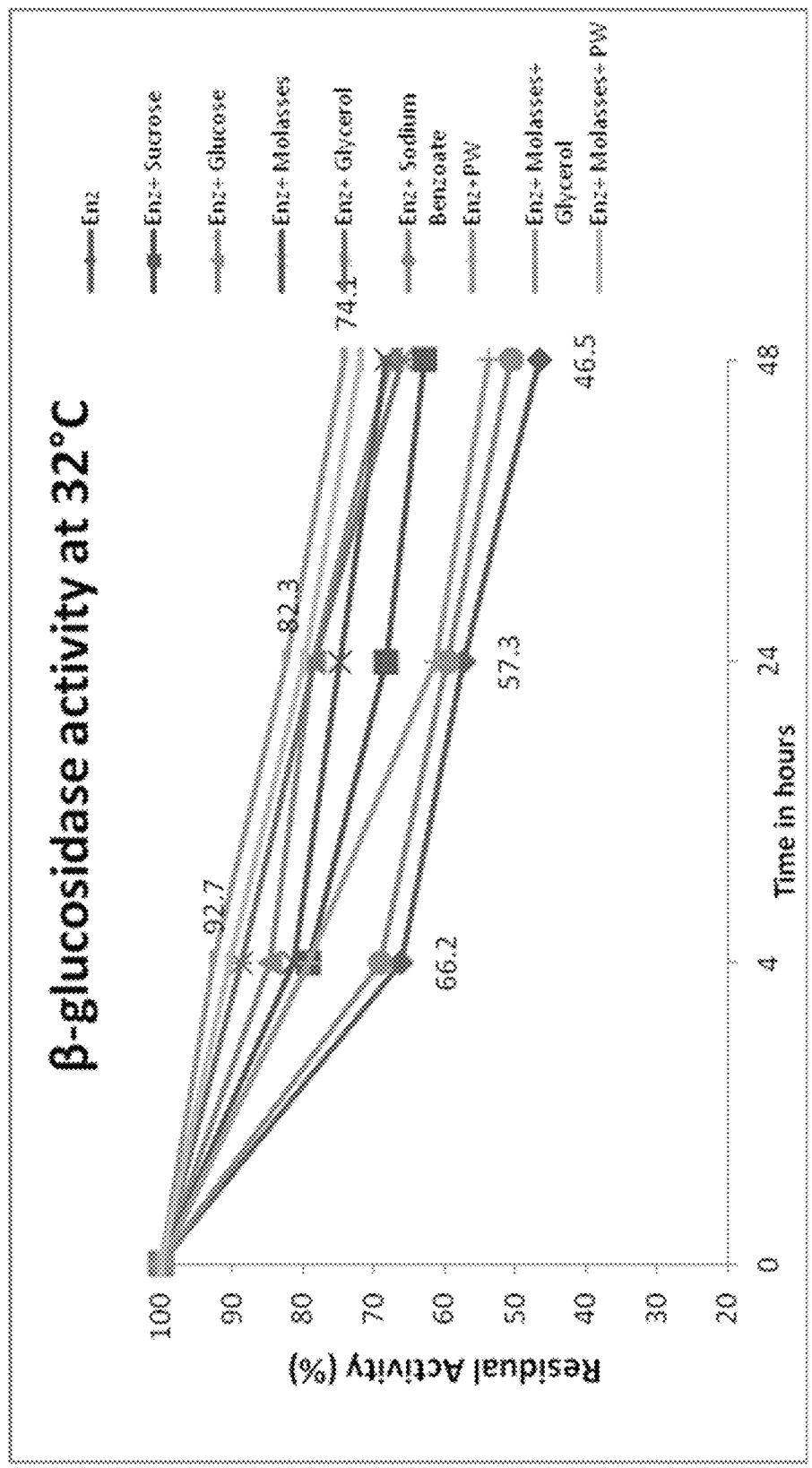
FIG. 1(b) illustrates graphical representation of enzyme stability at ambient temperatures (32° C.) of β-glucosidase activity.
FIG. 1(c) illustrates graphical representation of enzyme stability at ambient temperatures (32° C.) of protein stability.
Figure 1:
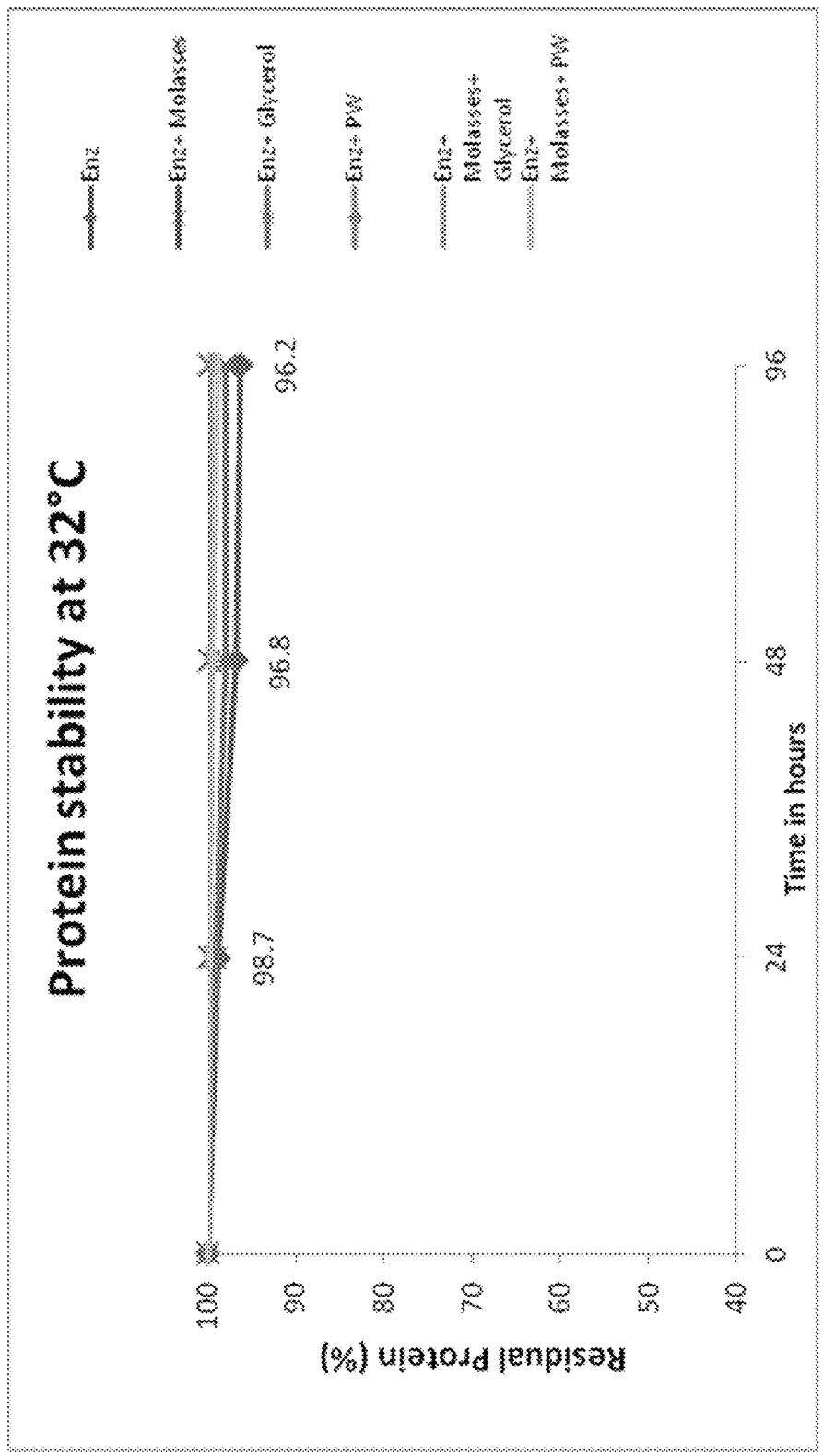

The present invention discloses a formulation to stabilize lignocellulolytic enzyme mixture. This invention in particular relates to a formulation composed of lignocellulolytic enzyme with critical dosages of molasses either with petrochemical waste or glycerol as an additive to improve enzyme stability in a synergistic manner. Specifically, the combination of petrochemical waste or glycerol with molasses as provided in the present invention synergistically improved the enzyme stability which can't be achieved with either of them alone. Maximum performance was achieved at total cellulase activity (FPU), beta-glucosidase activity and protein stability at operation temperature i.e. 50° C. and beta-glucosidase activity at ambient temperatures i.e. 32° C.

In accordance with the present invention, a formulation to stabilize lignocellulolytic enzyme mixture comprising an additive (10%-15% w/w) and molasses (5%-20% w/w). In an embodiment, the additive stream is comprised of a petrochemical waste (PW) stream. In yet another embodiment, the additive stream is comprised of glycerol.

In an embodiment of the present invention, there is provided a lignocellulolytic enzyme composition, said composition comprising:
 (a) 65% to 85% w/w lignocellulosic enzyme;
 (b) 10% to 15 w/w additive; and
 (c) 5% to 20% w/w molasses;
 Wherein; the additive is glycerol or a petrochemical waste stream.

In another embodiment of the present invention, the petrochemical waste stream comprises a mixture of MEG (0-0.5% w/w), DEG (0.5-30% w/w), TEG (40-50% w/w), TTEG (25-50% w/w), ethylene glycols having 5-12 monomeric units (1.3% w/w), and metals salts.

In yet another embodiment of the present invention, the metal salts are selected from the group consisting of sodium, chromium, boron, iron, and manganese.

In still another embodiment of the present invention, the molasses comprises at least 40% sugars.

In a further embodiment of the present invention, the sugar is selected from the group consisting of sucrose, glucose, and fructose.

In accordance with the present invention, a petrochemical waste (PW) stream comprising of a mixture of MEG (0-0.5%), DEG (0.5-30%), TEG (40-50%), TTEG (25-50%) other higher molecular weight ethylene glycols having 5-12 monomeric units (1.3%) and metals salts (10-6000 ppm). In accordance with the present invention, metals salts comprise Iron (Fe) is present at a concentration of 5842 ppm, sodium (Na) at 196 ppm, Chromium (Cr) at 126 ppm, Boron (B) at 112 ppm, manganese (Mn) at 78 ppm and others at concentrations <10 ppm.

In accordance with the present invention, the molasses used in the present invention must comprise of at least 40% sugars. The sugars comprising the molasses, used in accordance with the present invention include but are not limited to sucrose, glucose and fructose.

In an embodiment, petrochemical waste (PW) stream is sourced from naphtha to mono-ethylene glycol production unit of refinery. In yet another embodiment, the present invention may be used for stabilization of integrated on-site produced enzyme. In another, the present invention may be utilized for stabilization of enzyme off-site prior to introduction in the ethanol conversion process.

Having described the basic aspects of the present invention, the following non-limiting examples illustrate specific embodiment thereof.

EXAMPLES

Example 1

Lignocellulolytic Enzyme Analysis and Concentration

The analysis of lignocellulolytic enzyme mixture produced by *Aspergillus* sp. mutant was carried out to determine different enzyme components and activities like filter paper unit (FPU) for total cellulase activity, p-nitrophenyl-β-D-glucopyranosidase (pNPGase) activity for β-glucosidase (BGL), xylanase activity for hemicellulase and protein estimation by Bicinchoninic Acid assay (BCA). The analysis results are tabulated in Table 1.

Enzyme concentration is usually required to save the high costs involved during bulk enzyme ambient and shipping at refrigerated temperatures, improve the solid loadings during subsequent enzymatic hydrolysis experiments and removing undesired soluble/insoluble components like residual salts, degraded proteins and other metabolites. About 20 times concentration of raw lignocellulolytic enzyme was carried out by membrane based Tangential Flow Filtration unit having 10 KDa pore size. The analysis results are tabulated in Table 1. The concentrated enzyme broth was used for further experimental studies.

TABLE 1

Enzyme activity analysis of raw and concentrated enzyme mixture

| S. No. | Enzyme | Cellulase (FPU/ml) | β-glucosidase (BGL/ml) | Xylanase (U/ml) | Protein (mg/ml) |
|---|---|---|---|---|---|
| 1 | Native | 4.8 | 55 | 95 | 18 |
| 2 | Concentrated (20X) | 96 | 850 | 1300 | 350 |

Example 2

Screening of Stabilizers

Figure 2A:
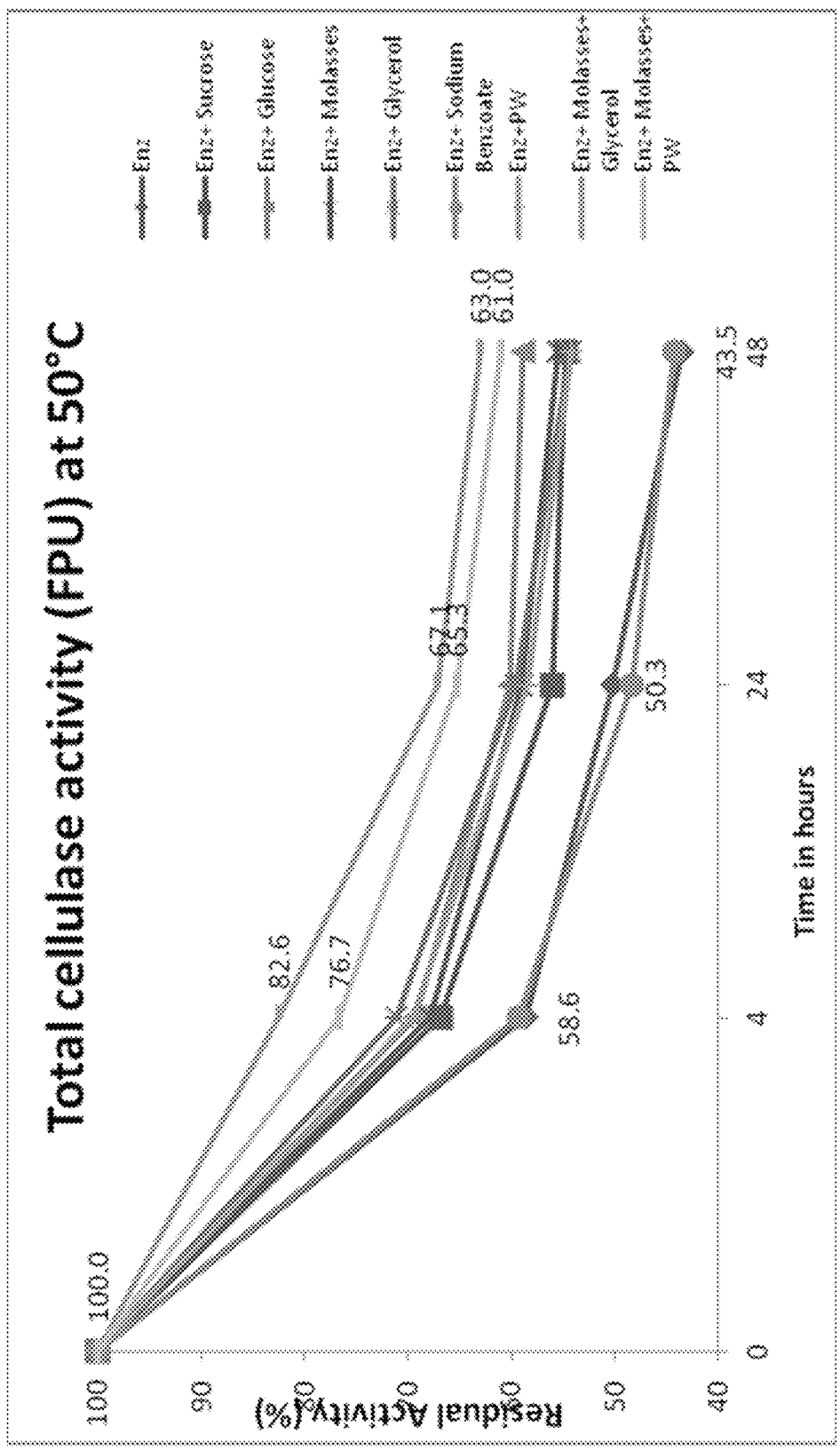
FIG. 2(a) illustrates graphical representation of enzyme stability at operational temperatures (50° C.) of total cellulase activity.

Different enzyme stabilizers viz. glucose, sucrose, glycerol, sodium benzoate, molasses and petrochemical waste (PW) stream from naphtha to mono-ethylene glycol production unit of refinery were evaluated both individually and in different combinations (Table 2) to improve the enzyme stability at ambient temperature i.e. 32° C. (FIGS. 1(a), 1(b), and 1(c)) and operational temperature i.e. 50° C. (FIGS. 2(a), 1(b), and 1(c)).

TABLE 2

Additive combinations and their compositions evaluated with enzyme

| S. No. | Additive combinations and composition (w/w) |
|---|---|
| 1 | Control without any stabilizer |
| 2 | Enzyme with (20%) Sucrose |
| 3 | Enzyme with (20%) Glucose |
| 4 | Enzyme with (20%) Molasses |
| 5 | Enzyme with (15%) Glycerol |
| 6 | Enzyme with (15%) Sodium benzoate |
| 7 | Enzyme with (15%) Petrochemical Waste (PW) |
| 8 | Enzyme with (20%) Molasses and (15%) Glycerol |
| 9 | Enzyme with (20%) Molasses and (15%) PW |

Figure 2B:
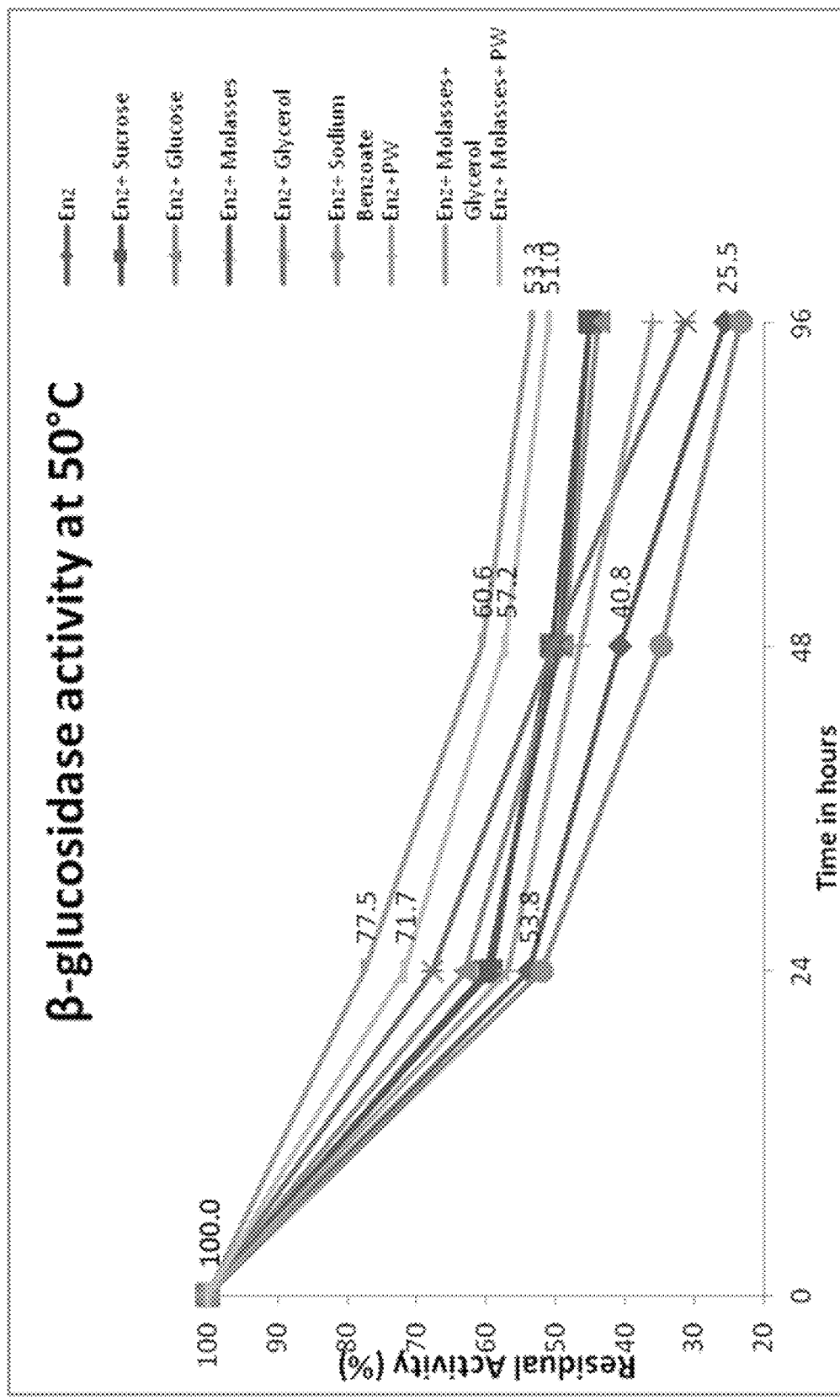
FIG. 2(b) illustrates graphical representation of enzyme stability at operational temperatures (50° C.) of β-glucosidase activity.
Figure 2C:
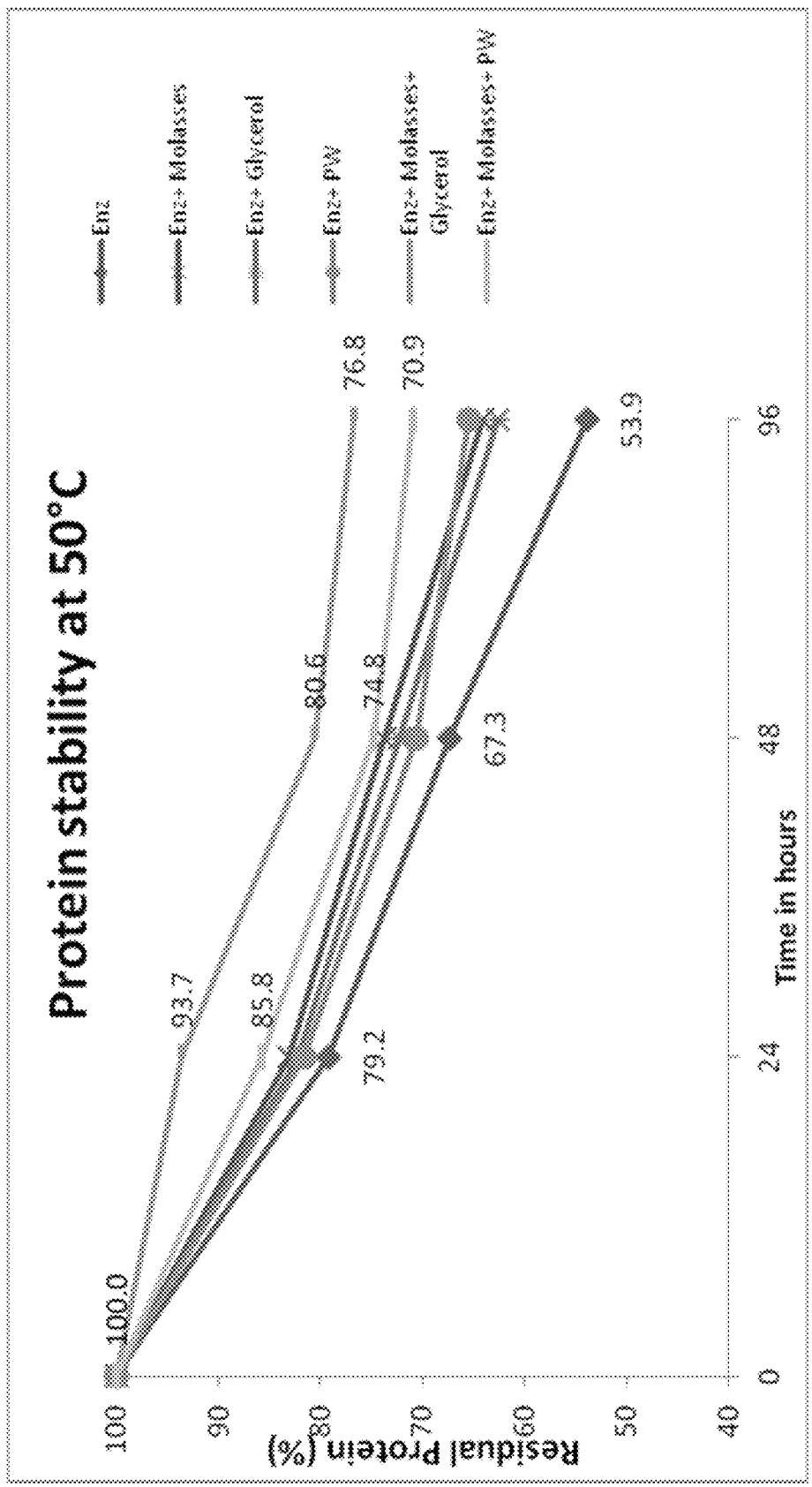
FIG. 2(c) illustrates graphical representation of enzyme stability at operational temperatures (50° C.) of protein stability.

The initial enzyme activity determined as cellulase activity by filter paper unit (FPU)/ml and β-glucosidase (BGL/ml) were considered as reference to study the effect of stabilizer formulations. The initial activity of each enzyme sample with stabilizer formulation and without stabilizer as control were considered as 100% and their residual activity is monitored continuously from 4 h to 96 h. The effect of stabilizers formulations on FPU, BGL activities and protein at ambient temperature i.e. 32° C. are depicted on FIG. 1a, 1b and 1c, respectively. While the effect of stabilizers formulations on FPU, BGL activities and protein at operational temperature of 50° C. are depicted on FIGS. 2a, 2b and 2c.

The results showed that PW with molasses and glycerol with molasses act synergistically to improve the enzyme stability as depicted by enzyme activities i.e. FPU and BGL at ambient temperature i.e. 32° C. and operational stability at 50° C. temperatures.

Both of the enzyme formulations also reduced the enzyme degradation as depicted by protein estimation.

What is claimed is:

1. A lignocellulolytic enzyme composition, said composition comprising:
    (a) 65% to 85% w/w lignocellulolytic enzyme mixture having a cellulase activity of 96 Filter Paper Unit (FPU)/ml, a β-glucosidase activity of about 850 β-glucosidase (BGL)/ml, a xylanase activity of about 1300 Units (U)/ml and a protein content of about 350 mg/ml;
    (b) 10% to 15% w/w additive; and
    (c) 5% to 20% w/w molasses;
wherein the additive is a petrochemical waste stream comprising 0-0.5% w/w MEG (mono-ethylene glycol), 0.5-30% w/w DEG (di-ethylene glycol), 40-50% w/w TEG (tri-ethylene glycol), 25-50% w/w TTEG (tetra-ethylene glycol), 1.3% w/w ethylene glycols having 5-12 monomeric units, 5842 ppm of iron, 196 ppm sodium, 126 ppm chromium, 112 ppm boron, and 78 ppm of manganese.

2. The lignocellulolytic enzyme composition as claimed in claim 1, wherein the molasses comprises at least 40% sugars.

3. The lignocellulolytic enzyme composition as claimed in claim 2, wherein the sugar is selected from the group consisting of sucrose, glucose, and fructose.

* * * * *